United States Patent
Hwang et al.

(10) Patent No.: US 7,816,315 B2
(45) Date of Patent: *Oct. 19, 2010

(54) METHOD OF ISOLATING A NUCLEIC ACID USING A MATERIAL CONTAINING AN AMINO GROUP AND A CARBOXYL GROUP AND POSITIVELY CHARGED AT A FIRST PH AND A SOLID MATERIAL FOR NUCLEIC ACID ISOLATION USED FOR THE METHOD

(75) Inventors: Kyu-youn Hwang, Incheon-si (KR); Chang-eun Yoo, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/208,884

(22) Filed: Sep. 11, 2008

(65) Prior Publication Data

US 2009/0012302 A1    Jan. 8, 2009

Related U.S. Application Data

(63) Continuation of application No. 11/401,794, filed on Apr. 11, 2006, now Pat. No. 7,439,023.

(30) Foreign Application Priority Data

Apr. 12, 2005 (KR) .................... 10-2005-0030286

(51) Int. Cl.
*A01N 61/00* (2006.01)
*A01N 65/00* (2009.01)
*A01N 57/00* (2006.01)
*C12Q 1/68* (2006.01)
*C07H 21/02* (2006.01)

(52) U.S. Cl. .............. 514/1; 514/68; 514/79; 435/6; 435/7.1; 435/7.2; 536/23.1

(58) Field of Classification Search ............. 435/6, 435/7.1, 7.2; 536/23.1; 514/1, 68, 79
See application file for complete search history.

(56) References Cited

U.S. PATENT DOCUMENTS

| 6,310,199 | B1 | 10/2001 | Smith et al. |
| 6,737,235 | B1 | 5/2004 | Cros et al. |
| 7,439,023 | B2 * | 10/2008 | Hwang et al. .............. 435/6 |
| 2001/0018513 | A1 | 8/2001 | Baker |

FOREIGN PATENT DOCUMENTS

| EP | 1473299 A2 | 11/2004 |
| JP | 2002-543979 A | 12/2002 |
| JP | 2004-521881 A | 7/2004 |
| WO | 0069872 | 11/2000 |

OTHER PUBLICATIONS

Reddy. Journal of Applied Polymer Science, vol. 75, 1721-1727, 2000.*
European Search Report dated Jul. 21, 2006 for Application No. 06007124.8 (All references cited in Search Report are cited above).

* cited by examiner

*Primary Examiner*—Jezia Riley
(74) *Attorney, Agent, or Firm*—Cantor Colburn LLP

(57) ABSTRACT

Provided are a method of isolating a nucleic acid from a sample and a solid material for isolating the nucleic acid which can be used for the above method. The method includes contacting the sample with a bifunctional material containing an amino group and a carboxyl group at a first pH to bind the nucleic acid to the bifunctional material, the bifunctional material being positively charged at the first pH; and releasing the nucleic acid at a second pH which is higher than the first pH.

9 Claims, No Drawings

METHOD OF ISOLATING A NUCLEIC ACID USING A MATERIAL CONTAINING AN AMINO GROUP AND A CARBOXYL GROUP AND POSITIVELY CHARGED AT A FIRST PH AND A SOLID MATERIAL FOR NUCLEIC ACID ISOLATION USED FOR THE METHOD

CROSS-REFERENCE TO RELATED PATENT APPLICATION

This application claims the benefit of Korean Patent Application No. 10-2005-0030286, filed on Apr. 12, 2005, in the Korean Intellectual Property Office, the disclosure of which is incorporated herein in its entirety by reference. This application is a continuation of application Ser. No. 11/401,794 filed Apr. 11, 2006 and is incorporated by reference in its entirety.

BACKGROUND OF THE INVENTION

1. Field of the Invention

The present invention relates to a method of isolating a nucleic acid using a material containing an amino group and a carboxyl group and positively charged at a first pH and to a solid material for isolating a nucleic acid which can be used for the method.

2. Description of the Related Art

Methods of isolating nucleic acids using pH dependent ion exchange matrices are known. For example, U.S. published patent application No. 2001/0018513 describes a method of isolating a nucleic acid using a material containing an ionisable group which is positively charged at a first pH such that it can be bound to the nucleic acid and releasing the nucleic acid at a second pH which is higher than the first pH. Examples of the material containing an ionisable group include N-2-acetamido-2-aminoethanesulfonic acid (ACES), N-2-acetamido-2-imidodiacetic acid (ADA), N-trihydroxymethyl-methyl-2-aminoethanesulfonic acid (TES) and trihydroxymethylaminoethane (Tris), etc. U.S. Pat. No. 6,310,199 describes a method of isolating a nucleic acid using a pH dependent ion exchange, the matrix comprising a silica magnetic particle and a plurality of first ion exchange ligands, each first ion exchange ligand comprising an aromatic hydrocarbon ring, a spacer covalently attached to the aromatic hydrocarbon ring, and a linker comprising a linker alkyl chain attached to the silica magnetic particle at its first end and attached to the spacer at its second end.

However, there is still a need for materials a containing ionisable group which can bind to the nucleic acids at a high speed and have a high efficiency of releasing the nucleic aids when pH is increased, even using the above methods.

Thus, the inventors of the present invention searched for materials which can bind to the nucleic acids at a higher speed to adsorb the nucleic acids more rapidly and have a remarkably high efficiency of releasing the nucleic aids when pH is increased, and discovered bifunctional materials containing both an amino group and a carboxyl group.

SUMMARY OF THE INVENTION

The present invention provides a method of rapidly isolating a nucleic acid in a high efficiency, using a material which binds to the nucleic acid at a high speed and has a high efficiency of releasing the nucleic aid when pH is increased.

The present invention also provides a solid material for isolating a nucleic acid which can be used for the above method.

According to an aspect of the present invention, there is provided a method of isolating a nucleic acid from a sample comprising the nucleic acid, comprising: contacting the sample with a bifunctional material containing an amino group and a carboxyl group at a first pH to bind the nucleic acid to the bifunctional material, the bifunctional material being positively charged at the first pH; and releasing the nucleic acid at a second pH which is higher than the first pH, wherein the bifunctional material has formula 1 or 2,

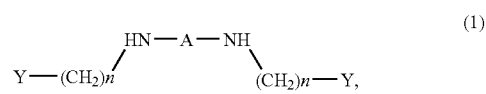

wherein
n is an integer from 1 to 10,
A is

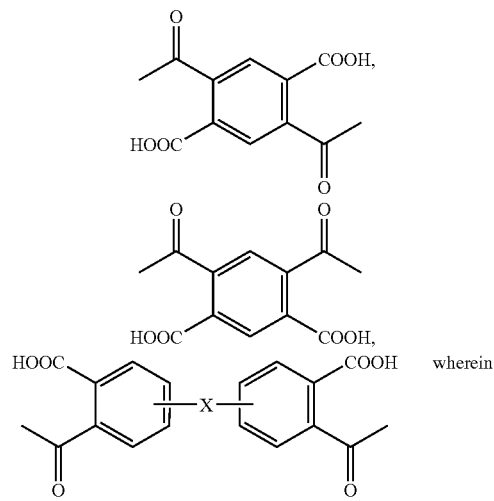

x is O, CO, S, $SO_2$, $CH_2$, $C(CH_3)_2$ or $C(CF_3)_2$,

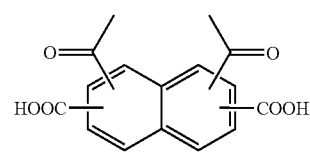

(wherein a carbonyl group and a carboxyl group may be substituted on any carbon position except for a linking portion of the rings),

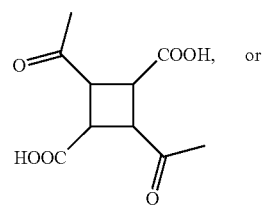

-continued

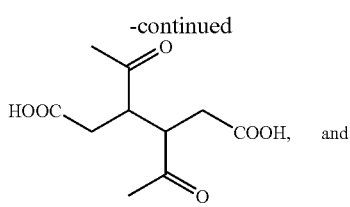

Y is a nitrogen-containing heterocyclic base,

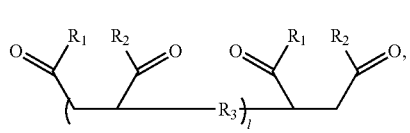
(2)

wherein $R_1$ and $R_2$ may be identical or different and each independently selected from the group consisting of a —OH group and a —NH(CH$_2$)$_n$Y group, wherein n and Y are as defined above, $R_3$ is a $C_{1-10}$ alkyl group, and l is an integer from 1 to 30,000.

The above and other features and advantages of the present invention will become more apparent by describing in detail exemplary embodiments thereof.

DETAILED DESCRIPTION OF THE INVENTION

In formula 1, A is a derivative of tetracarboxylic acid dianhydride containing two carboxyl groups and two carbonyl groups, selected from the group consisting of pyromellitic dianhydride, 3,3',4,4'-biphenyltetracarboxylic dianhydride, 2,2',3,3'-biphenyltetracarboxylic dianhydride, 2,3,3',4'-biphenyltetracarboxylic dianhydride, 1,2,4,5-benzenetetracarboxylic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, bis(3,4-dicarboxyphenyl)ether dianhydride, bis(3,4-dicarboxyphenyl)sulfone dianhydride, 1,4,5,8-naphthalenetetracarboxylic dianhydride, 1,2,5,6-naphthalenetetracarboxylic dianhydride, 2,3,6,7-naphthalenetetracarboxylic dianhydride, 2,2-bis(3,4-dicarboxyphenyl)-hexafluoropropane dianhydride, cyclobutanetetracarboxylic dianhydride, methylcyclobutanetetracarboxylic dianhydride, and 1,2,3,4-tetracarboxybutane dianhydride, wherein each carbonyl group may be bound to —NH.

In formula 1, Y is a nitrogen-containing heterocyclic base. Y may be selected from the group consisting of a pyridinyl group and an imidazolyl group, but is not limited thereto.

In formula 2, when $R_1$ and/or $R_2$ is a —NH(CH$_2$)$_n$Y group wherein Y is a nitrogen-containing heterocyclic base, Y may be selected from the group consisting of a pyridinyl group and an imidazolyl group, but is not limited thereto.

According to an embodiment of the present invention, the method includes contacting the sample with a bifunctional material containing an amino group and a carboxyl group at a first pH to bind the nucleic acid to the bifunctional material, the bifunctional material being positively charged at the first pH. The sample comprises a nucleic acid, and examples of the sample include a biological sample, such as blood and a solution containing cells, and a nucleic acid solution, such as a solution containing PCR products.

According to an embodiment of the present invention, the material to which the nucleic acid in the sample is bound is a bifunctional material containing an amino group and a carboxyl group and positively charged at the first pH. The material may be a compound itself or a solid material having these functional groups immobilized on a solid substrate. The solid substrate may be selected from the group consisting of silicone, glass, and plastic materials, but is not limited thereto.

According to an exemplary embodiment of the present invention, the material may have formula 1, wherein n is an integer from 1 to 10, A is

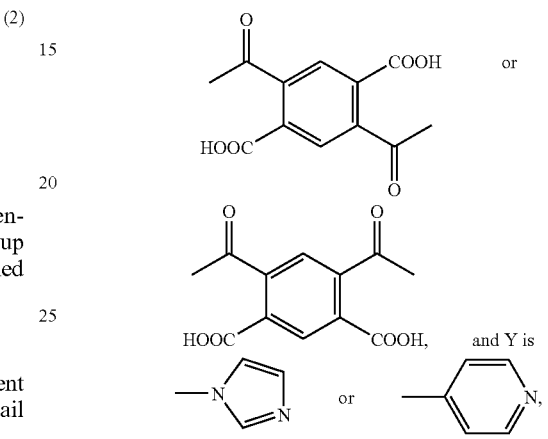

or formula 2, wherein $R_1$ and $R_2$ may be identical or different and each independently selected from the group consisting of a —OH group and a —NH(CH$_2$)$_n$Y, wherein n and Y are as defined above, $R_3$ is a $C_{1-10}$ alkyl group, and l is an integer from 1 to 30,000.

More preferably, the material may have formula 1, wherein n is an integer from 1 to 3, A is

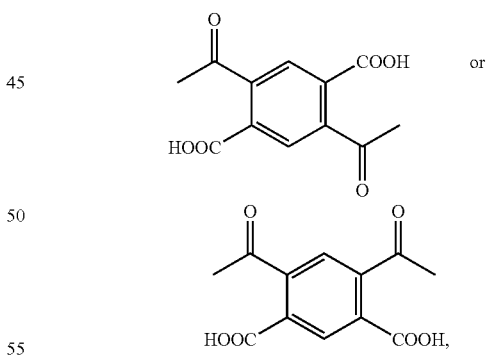

and Y is

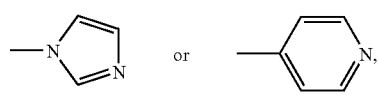

or formula 2, wherein $R_1$ and $R_2$ may be identical or different and each independently selected from the group consisting of a —OH group and a —NH(CH$_2$)$_n$Y, wherein n and Y are as defined above, R$_3$ is a C$_{1-10}$ alkyl group, and I is an integer from 1 to 30,000.

The compounds having formulae 1 and 2 contain an amino group and a carboxyl group. In the compound having formula 1, a ratio of a positive charge to a negative charge may be about 2:1 at the first PH. In the compound having formula 2, a ratio of the —OH group to the —NH(CH$_2$)$_n$Y group wherein n is an integer from 1 to 10 and Y is a nitrogen-containing heterocyclic base group may be about 2:1.

According to an embodiment of the present invention, the compound having formula 1 may be obtained by reacting tetracarboxylic acid dianhydride, such as 1,2,4,5-benzene tetracarboxylic acid dianhydride with NH$_2$(CH$_2$)$_n$Y, wherein n is an integer from 1 to 10 and Y is a nitrogen-containing heterocyclic base, such as 4-(aminomethyl)pyridine or 1-(3-aminopropyl)imidazole. Further, the compound having formula 2 may be obtained by reacting a compound having formula 3 with NH$_2$(CH$_2$)$_n$Y wherein n is an integer from 1 to 10 and Y is a nitrogen-containing heterocyclic base. The ratio of the —OH group to the —NH(CH$_2$)$_n$Y group in the resulting compound having formula 2 may be adjusted by controlling a concentration of NH$_2$(CH$_2$)$_n$Y in the reaction mixture.

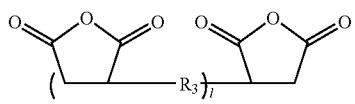

(3)

wherein
R$_3$ is a C$_{1-10}$ alkyl group, and
I is an integer from 1 to 30,000.

The compound having formula 3 may be a compound having formula 4.

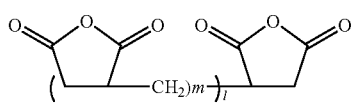

(4)

wherein
m is an integer from 1 to 10, and
I is an integer from 1 to 30,000.

The compound having formula 3 is a polyanhydride polymer. The polymer can easily be isolated from a solution using an isolation process, for example, centrifugation. Thus, the nucleic acid may be easily isolated from the polymer of formula 2 by binding the nucleic acid to the polymer of formula 2 obtained from the polymer of formula 3, isolating the resultant nucleic acid-polymer from the solution, and eluting the isolated nucleic acid-polymer at the second pH.

According to another exemplary embodiment of the present invention, the material is a solid material having a group having formula 5 or 6 immobilized on a solid substrate:

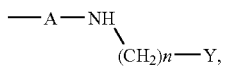

(5)

wherein
n, A, and Y are defined as in formula 1,

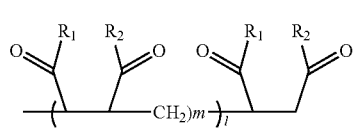

(6)

wherein
R$_1$, R$_2$, and I are defined as in formula 2, and
m is an integer from 1 to 10.

Examples of the group having formula 5 or 6 may include a group having formula 5, wherein n is an integer from 1 10, A is

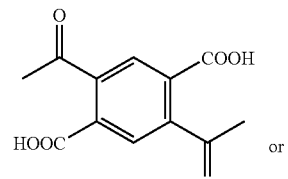

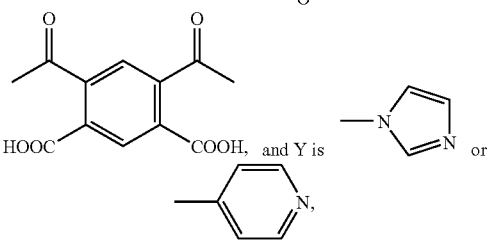
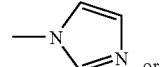

or a group having formula 6, wherein R$_1$ and R$_2$ may be identical or different and each independently selected from the group consisting of a —OH group and a —NH(CH$_2$)$_n$Y, wherein n is an integer from 1 to 10 and Y is

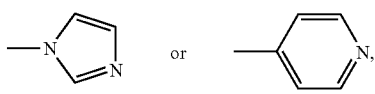

R$_3$ is a C1-10 alkyl group, I is an integer from 1 to 30,000. More preferably, in formula 6, R$_1$ and R$_2$ may be identical or different and each independently selected from the group consisting of a —OH group and a —NH(CH$_2$)$_n$Y, wherein n is an integer from 1 to 10, Y is

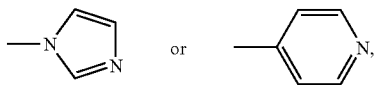

R$_3$ is a C1-10 alkyl group, I is an integer from 1 to 30,000, a ratio of the —OH group to the —NH(CH$_2$)$_n$Y group being about 2:1.

In the present exemplary embodiment, the solid substrate may be selected from the group consisting of silicone, glass, and plastic materials, but is not limited thereto. Further, the solid substrate may be activated such that the group having formula 5 or 6 is immobilized thereon. For example, the solid substrate may be coated with an active group, such as an amino group.

According to an embodiment of the present invention, the solid material having the group having formula 5 or 6 immobilized on a solid substrate may be produced using any immobilization method which is known in the art. For example, the solid material may be produced by reacting tetracarboxylic acid dianhydride, such as 1,2,4,5-benzene tetracarboxylic acid dianhydride with a solid substrate (for example, silicone, glass, or plastic materials) coated with an amino group, such as $NH_2(CH_2)_nNH_2$, to immobilize it on the substrate, and then, reacting a compound of $NH_2(CH_2)_nY$, wherein n is an integer from 1 to 10 and Y is a nitrogen-containing heterocyclic base (for example, 4-(aminomethyl)pyridine or 1-(3-aminopropyl)imidazole) with the resultant solid substrate. Further, the solid material having a functional group having formula 6 immobilized thereon may be produced, for example, by reacting the polyanhydride having formula 3 with a substrate coated with an amino group to immobilize the functional group on the substrate, and then, reacting a compound of $NH_2(CH_2)_nY$ wherein n is an integer from 1 to 10 and Y is a nitrogen-containing heterocyclic base (for example, 4-(aminomethyl)pyridine or 1-(3-aminopropyl)imidazole) with the resultant solid substrate.

According to an embodiment of the present invention, the first pH may be less than a $pK_a$ value of a carboxyl group in the compounds having formulae 1 and 2 or the groups having formulae 5 and 6. Specifically, the first pH may be 2-3.5, but is not limited thereto.

The method according to an embodiment of the present invention includes isolating the nucleic acid from the resultant material-nucleic acid at the second pH which is higher than the first pH. The isolation of the nucleic acid includes isolating the nucleic acid-bifunctional material complex from the mixture and eluting the complex with a solution having the second pH.

The second pH may be any pH that is higher than the first pH, and preferably may 5-10. The solution used for eluting the nucleic acid-bifunctional material complex may be water or a buffer, etc.

According to another embodiment of the present invention, there is provided a solid material having a group having formula 5 or 6 immobilized on a solid substrate:

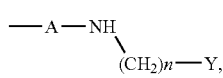 (5)

wherein
n, A, and Y are as defined above,

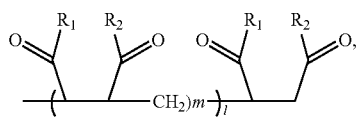 (6)

wherein
$R_1$, $R_2$, m, and l are as defined above.

The solid substrate includes any solid materials. The solid material may be selected from the group consisting of silicone, glass, and plastic materials. The solid substrate may have any form. For example, the solid substrate may be in a form of sphere, plate, or may be amorphous, but is not limited thereto.

According to an exemplary embodiment of the present invention, in formula 6, $R_1$ and $R_2$ may be identical or different and each independently selected from the group consisting of a —OH group and a —$NH(CH_2)_nY$ group, wherein n is an integer from 1 to 10 and Y is

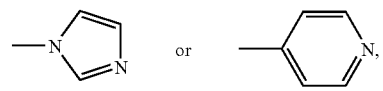

$R_3$ is a $C_{1-10}$ alkyl group, and I is an integer from 1 to 30,000, a ratio of the —OH group to the —$NH(CH_2)_nY$ group being about 2:1.

The solid material for isolating a nucleic acid according to an embodiment of the present invention is positively charged at the first pH and negatively charged at the second pH. In addition, the solid material has a characteristic of rapidly binding to the nucleic acid at the first pH and releasing the nucleic acid at the second pH in a high efficiency. Thus, the solid material can be useful in isolating the nucleic acid from the sample.

Hereinafter, the present invention will be described in more detail with reference to the following examples. However, these examples are given for the purpose of illustration and are not intended to limit the scope of the invention.

EXAMPLES

Example 1

Recovery of Nucleic Acid Using a Substrate Having a Group of Formula 6 Immobilized Thereon In Example 1, a substrate having a group of formula 6 immobilized thereon was prepared and DNAs were bound to the substrate at a first pH and then, the nucleic acids were recovered from the DNA-substrate complex at a second pH.

The group of formula 6 used in this Example has the following formula:

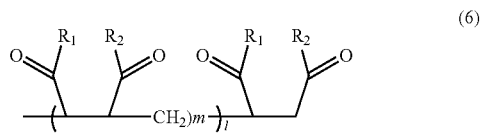 (6)

wherein
$R_1$ and $R_2$ may be identical or different and each independently selected from the group consisting of a —OH group and a —$NH(CH_2)_2NH_2$ group (control), 4-(aminomethyl)pyridinyl (test 1) or 1-(3-aminopropyl)imidazolyl (test 2),
m is 2, and
I is from 1 to 30,000.

In formula 6, a ratio of an amino group to a carbonyl group in $R_1$ and $R_2$ was controlled according to conditions of the reaction in which —$NH(CH_2)_2NH_2$, 4-(aminomethyl)pyridinyl or 1-(3-aminopropyl)imidazolyl group was introduced.

Immobilization of the functional group having formula 6 on the substrate was performed as follows. First, a glass substrate coated with an amino group (Corning GAPS glass, Corning Corporation) was immersed in 200 mM (based on a repeat unit) polyanhydride (Poly(ethylene-alt-maleic anhydride)) (molecular weight (Mw)=100,000-500,0000) in N-methyl-2-pyrolidone (NMP) at room temperature for 1 hour, and then the substrate was washed with acetone and dried in a vacuum. The resultant glass substrate having polyanhydride bound thereto was immersed in ethylene diamine, 4-(aminomethyl)pyridine, or 1-(3-aminopropyl)imidazole in NMP (a molar ratio of ethylene diamine, 4-(aminomethyl) pyridine, or 1-(3-aminopropyl)imidazole:$H_2O$=4:6) at room temperature for 1 hour, and then the substrate was washed with acetone and dried. In the immersion, 400 mM of ethylene diamine, 4-(aminomethyl)pyridine, or 1-(3-aminopropyl)imidazole and 600 mM of water used.

A DNA having SEQ ID No. 1 labeled with Cy3 at a 5' end position was reacted with each of the resultant two glass substrates coated with the group of formula 6 at pH 3. The reaction was performed by adding a 0.15 M sodium acetate solution containing 1 µM of the DNA to a surface of each of the substrates, covering the substrate with a cover, and placing it at room temperature for 1 hour. After the reaction, the substrates were washed with 0.15 M sodium acetate at pH 3 and 7.9, respectively. Next, their fluorescent intensities were determined using Axon scanner (GenePix company, U.S.A.) at 532 nm (PMT 350). The results are shown in Table 1. A glass substrate coated with an amino group (Corning GAPS glass, Corning Corporation), which was not coated with the functional group having formula 6, was used as a control.

TABLE 1

| Substrate | Fluorescent Intensity | | Recovery (%) |
|---|---|---|---|
| | pH 3 | pH 7.9 | |
| Control | 17780 | 5995 | 66 |
| Test 1 | 18606 | 2375 | 87 |
| Test 2 | 20126 | 1020 | 95 |

As shown in Table 1, the substrates of test 1 and test 2 had a remarkably higher DNA recovery than the control substrate.

Example 2

Recovery of Nucleic Acids Using a Substrate Having a Group of Formula 6 Immobilized Thereon The experiment was performed in the same manner as in Example 1, except that after the DNA was bound to each of the substrates coated with the functional group of formula 6 at pH 3, the pH of the substrates was changed to pH 7.9.

The fluorescent intensities were determined. The results are shown in Table 2.

TABLE 2

| Substrate | Fluorescent Intensity | | Recovery (%) |
|---|---|---|---|
| | pH 3 | pH 7.9 | |
| Control 1 | 16032 | 9896 | 45 |
| | 17767 | 8696 | |
| | 16900 | 9296 | |
| Test 1 | 18437 | 8707 | 59 |
| | 17785 | 6073 | |
| | 18111 | 7390 | |
| Test 2 | 17893 | 3158 | 83 |
| | 18543 | 2995 | |
| | 18218 | 3077 | |

As shown in Table 2, the substrates of test 1 and test 2 had a remarkably higher DNA recovery than the substrate of control 1.

By using a method of isolating a nucleic acid according to the present invention, the nucleic acid can be more rapidly isolated in a higher efficiency.

By using a solid substrate according to an embodiment of the present invention, a surface which can more rapidly isolate the nucleic acid in a higher efficiency may be provided.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound comprising:
   a bifunctional material containing an amino group and a carboxyl group,
   wherein the bifunctional material has formula 1 or 2,

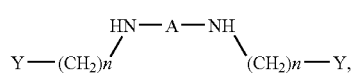

wherein n is an integer from 1 to 10,

A is

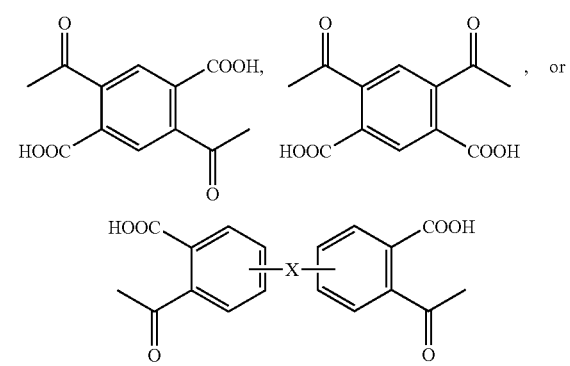

wherein x is O, CO, S, $SO_2$, $CH_2$, $C(CH_3)_2$ or $C(CF_3)_2$, or

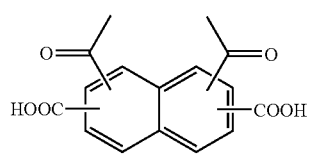

wherein a carbonyl group and a carboxyl group may be substituted on any carbon position except for a linking portion of the rings,

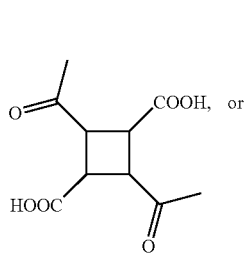

and Y is

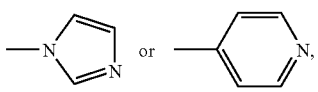

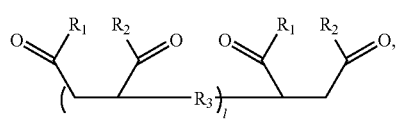

wherein $R_1$ and $R_2$ may be identical or different and each is independently selected from the group consisting of a —OH group and a —NH(CH$_2$)$_n$Y group, wherein n is an integer from 1 to 10 and Y is a nitrogen containing heterocycle base, $R_3$ is a $C_{1-10}$ alkyl group, and l is an integer from 1 to 30,000.

2. The compound of claim 1, wherein the material has formula 1, wherein n is an integer from 1 to 10, A is

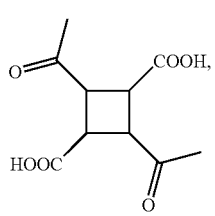 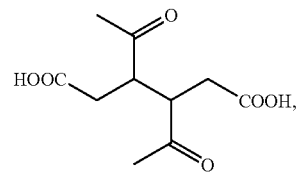

or formula 2, wherein $R_1$ and $R_2$ may be identical or different and each independently selected from the group consisting of a —OH group and a —NH(CH$_2$)$_n$Y, wherein n is an integer from 1 to 10 and Y is a nitrogen containing heterocycle base, $R_3$ is a $C_{1-10}$ alkyl group, and l is an integer from 1 to 30,000.

3. The compound of claim 1, wherein the bifunctional material has formula 2, wherein $R_1$ and $R_2$ may be identical or different and each independently selected from the group consisting of a —OH group and a —NH(CH$_2$)$_n$Y group, wherein n is an integer from 1 to 10 and Y is

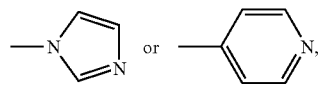

$R_3$ is a $C_{1-10}$ alkyl group, and l is an integer from 1 to 30,000, a ratio of the —OH group to the —NH(CH$_2$)$_n$Y group being about 2:1.

4. The compound of claim 1, wherein formula 1, A is a derivative of tetracarboxylic acid dianhydride containing two carboxyl groups and two carbonyl groups, wherein tetracarboxylic acid dianhydride is selected from the group consisting of pyromellitic dianhydride, 3,3',4,4'-biphenyltetracarboxylic dianhydride, 2,2',3,3'-biphenyltetracarboxylic dianhydride, 2,3,3',4'-biphenyltetracarboxylic dianhydride, 1,2,4,5-benzenetetracarboxylic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, bis(3,4-dicarboxyphenyl)ether dianhydride, bis(3,4-dicarboxyphenyl)sulfone dianhydride, 1,4,5,8-naphthalenetetracarboxylic dianhydride, 1,2,5,6-naphthalenetetracarboxylic dianhydride, 2,3,6,7-naphthalenetetracarboxylic dianhydride, 2,2-bis(3,4-dicarboxyphenyl)-hexafluoropropane dianhydride, cyclobutanetetracarboxylic dianhydride, methylcyclobutanetetracarboxylic dianhydride, and 1,2,3,4-tetracarboxybutane dianhydride, wherein each carbonyl group is bound to —NH.

5. The compound of claim 1, wherein the compound is a solid material having a group having formula 5 or 6:

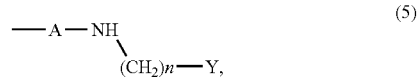

wherein n, A, and Y are defined as in formula 1,

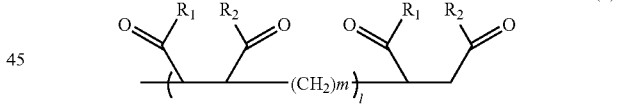

wherein $R_1$, $R_2$, and l are defined as in formula 2, and m is an integer from 1 to 10.

6. The compound of claim 5, wherein in formula 6, $R_1$ and $R_2$ may be identical or different and each independently selected from the group consisting of a —OH group and a —NH(CH$_2$)$_n$Y group, wherein n is an integer from 1 to 10 and Y is

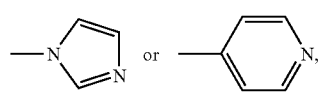

$R_3$ is a $C_{1-10}$ alkyl group, and l is an integer from 1 to 30,000, a ratio of the —OH group to the —NH(CH$_2$)$_n$Y group being about 2:1.

7. The compound of claim 1, wherein the compound is a solid material having a group having formula 5 or 6:

Y is

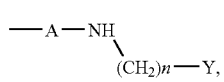  (5)

wherein n is an integer from 1 to 10,
A is

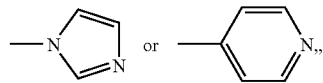 or

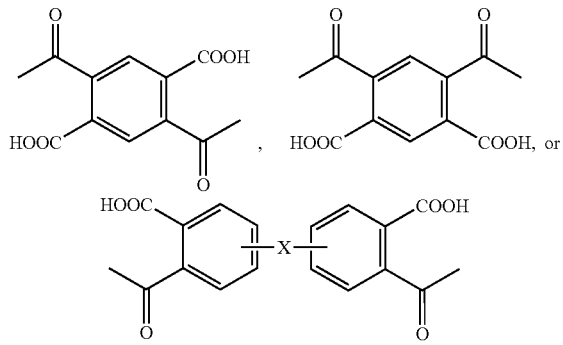

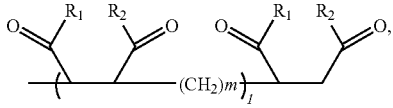  (6)

wherein $R_1$ and $R_2$ may be identical or different and each independently selected from the group consisting of a —OH group and a —NH(CH$_2$)$_n$Y group, wherein n is an integer from 1 to 10 and Y is a nitrogen containing heterocycle base, $R_3$ is a $C_{1-10}$ alkyl group, and l is an integer from 1 to 30,000, and m is an integer from 1 to 10.

8. The compound of claim 7, wherein in formula 6, $R_1$ and $R_2$ may be identical or different and each independently selected from the group consisting of a —OH group and a —NH(CH$_2$)$_n$Y group, wherein n is an integer from 1 to 10 and Y is wherein x is O, CO, S, SO$_2$, CH$_2$, C(CH$_3$)$_2$ or C(CF$_3$)$_2$, or

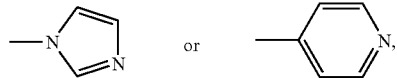 or

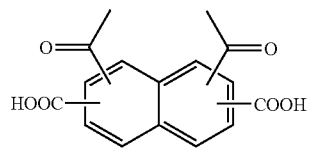

wherein a carbonyl group and a carboxyl group may be substituted on any carbon position except for a linking portion of the rings, $R_3$ is a $C_{1-10}$ alkyl group, and l is an integer from 1 to 30,000, a ratio of the —OH group to the —NH(CH$_2$)$_n$Y group being about 2:1.

9. A compound comprising: a bifunctional material containing an amino group and a carboxyl group, wherein the bifunctional material is the reaction product of a compound having formula 3 with NH$_2$(CH$_2$)nY wherein n is an integer from 1 to 10 and Y is a nitrogen-containing hetero ring base,

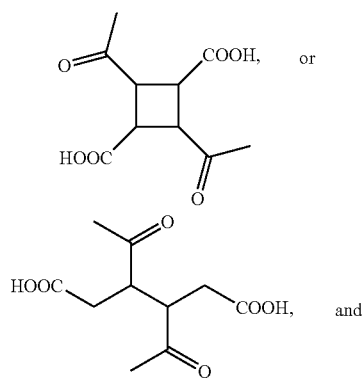

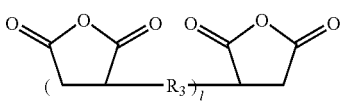  (3)

wherein $R_3$ is a $C_{1-10}$ alkyl group, and l is an integer from 1 to 30,000.

* * * * *